(12) United States Patent
Garin et al.

(10) Patent No.: US 7,044,707 B2
(45) Date of Patent: May 16, 2006

(54) MACHINE FOR DISPLACEMENT OF RECEPTACLES IN FRONT OF INSPECTION STATIONS

(75) Inventors: Jean-François Garin, Lyons (FR); Laurent Miranda De Azevedo, Lyons (FR)

(73) Assignee: BSN Glasspack, Villeurbanne (FR)

( * ) Notice: Subject to any disclaimer, the term of this patent is extended or adjusted under 35 U.S.C. 154(b) by 202 days.

(21) Appl. No.: 10/691,666

(22) Filed: Oct. 24, 2003

(65) Prior Publication Data

US 2004/0129614 A1    Jul. 8, 2004

(30) Foreign Application Priority Data

Oct. 25, 2002    (FR) .................................. 02 13360

(51) Int. Cl.
*B65G 57/14* (2006.01)

(52) U.S. Cl. .................................. 414/749.1; 198/626.1
(58) Field of Classification Search ............. 414/749.1, 414/222; 198/339.1, 626.1, 817, 980
See application file for complete search history.

(56) References Cited

U.S. PATENT DOCUMENTS

| | | | |
|---|---|---|---|
| 4,015,722 A | * | 4/1977 | Cooper et al. ........... 414/788.2 |
| 4,077,254 A | | 3/1978 | Mercer, Jr. et al. |
| 5,505,312 A | | 4/1996 | Haring et al. |
| 2002/0070097 A1 | * | 6/2002 | Ritter et al. ................ 198/626 |

FOREIGN PATENT DOCUMENTS

| | | |
|---|---|---|
| DE | G8903180.6 | 6/1989 |
| EP | 0 897 760 A1 | 2/1999 |
| JP | A 62-16920 | 1/1987 |

* cited by examiner

*Primary Examiner*—Donald W. Underwood
(74) *Attorney, Agent, or Firm*—Clark & Brody

(57) ABSTRACT

The machine according to the invention comprises:
- a lower frame fitted with a linear guide system (21),
- a mobile carriage (23) comprising a front half-carriage (24) and a back half-carriage (25), each half-carriage including:
  - a rigid bridge installed free to slide on the linear guide systems (21),
  - a motorised device (37) for driving at least one belt in rotation,
  - at least a first return device (41) for at least one belt,
  - at least one endless driving belt (38) installed between the motorised drive device (37) and the return device (41) and delimiting a receptacle gripping and movement path,
- and a system (61) for moving one half-carriage away from or towards the other half-carriage.

27 Claims, 8 Drawing Sheets

MACHINE FOR DISPLACEMENT OF RECEPTACLES IN FRONT OF INSPECTION STATIONS

The invention relates to the technical domain of machines moving receptacles in front of at least one, and more generally a series of receptacle checking and/or inspection stations.

One particularly advantageous application of said invention is in the domain of checking or inspection of transparent or translucid receptacles, for example such as glass bottles, pots or jars.

In this technical domain, a machine moving receptacles in front of different checking stations is usually provided with a frame equipped with a drive system consisting of endless belts installed facing each other, so as to define a path for gripping receptacles and moving them from one end of the belts to the other. During said movement, these receptacles supported on the frame pass in sequence in front of different check and/or inspection stations, usually optical stations. Since said type of machine is designed to move different diameters of receptacles, the belts are installed free to move away from each other or towards each other so that the width of the receptacle gripping and displacement path can be adjusted.

Conventionally, said type of machine is included on a receptacle conveyor path forming part of a manufacturing and/or packaging line. Therefore, the conveyor line needs to be interrupted so that a displacement and checking machine can be inserted, as described above. Industrial and particularly economic constraints make it essential that the size of the displacement and checking machine should be as small as possible, while including as many detection stations as possible. The size of the means used to move different sizes of receptacles is non-negligible, which limits the number of checking stations that can be installed, or makes it necessary to install a large number of mechanical, electrical and optical equipment units in a small space. In particular, said small amount of space makes it difficult to carry out repair, maintenance or cleaning work, for example when receptacles break and make the various components of the machine dirty.

The state of the art also includes a receptacle conveying machine comprising a first single movement path section and a second multiple movement paths section, as divulged in patent application EP 0 897 760.

Said type of machine comprises a deviation conveyor shaped so as to transfer receptacles from the first movement path section to the second multiple paths movement section.

Said deviation conveyor is designed so that receptacles are suspended as they are moved, without being supported on their bottom.

Said type of deviation conveyor is installed in parallel with the main conveyor such that receptacles follow a non-linear path, which limits the receptacle displacement speed and complicates handling of non-cylindrical receptacles. Therefore, said type of machine is not suitable for insertion on a conveyor line forming part of a manufacturing and/or packaging line.

Therefore, there is a need for such a machine designed for the displacement of different sizes of receptacles over a limited length of a conveyor line, leaving the receptacle displacement environment free, so that as many check or inspection stations as possible can be installed.

Therefore, the purpose of the invention is to overcome the disadvantages mentioned above by describing a compact machine designed to be integrated on a conveyor line, such that different sizes of receptacles can be moved in front of a series of detection and/or checking stations.

Another purpose of the invention is a machine designed to facilitate access to the environment of the receptacle displacement area.

In order to achieve said objective, the machine according to the invention comprises:
  a lower frame, supporting a front half-carriage and a back half-carriage extending along longitudinal planes parallel to each other, each half-carriage comprising:
    a motorised device driving at least one belt in rotation, the motorised drive device being located at a first end of the half-carriage,
    at least one return device for at least one belt, located at the second end of the half-carriage,
    at least one first endless drive belt installed between the motorised drive device and the return device, with one strand placed at a distance from the strand of the belt supported by the other half-carriage so as to delimit a receptacle gripping and movement path between them.

According to the invention:
  the lower frame has at least two transverse sides, one of which has a passage compartment for the end of a receptacle input conveyor that cooperates with a return head on the input side installed on the frame, while the other transverse side has a passage compartment for the end of a receptacle output conveyor that cooperates with a return head on the output side installed on the frame, and cooperating with the return head on the input side to delimit a volume interrupting the conveyance, each transverse side being provided with a linear guide system extending on the outside of the conveyance interruption volume,
  the machine comprises:
    a mobile carriage supported by linear guide systems and composed of the front half-carriage and the back half-carriage, each half-carriage comprising a rigid bridge installed at each end, and sliding on the linear guide systems,
    and a displacement system moving one half-carriage away from or towards the other half-carriage located outside the conveyance interruption volume.

According to one preferred characteristic of the embodiment, each half-carriage comprises a geared motor installed on the centre-line of the motorised drive device.

According to one characteristic of the embodiment, the machine comprises:
  a second return device for a belt, supported by the rigid bridge and being located at the second end of the said bridge and extending superposed from the first return device, each return device being composed of a pulley,
  a second endless drive belt between the motorised drive device and the second return device with one strand of the belt passing in front of a bearing plate supported by the rigid bridge and at a distance from a strand of the second belt supported by the other half-carriage,
  and a common drive drum driving the first and second belts.

Another purpose of the invention is a machine comprising a protection cladding and an access door so that an operator can use the man-machine interface, just as well in the open and closed position of the door.

In order to achieve said objective, the access door comprises a chassis delimiting an opening and equipped with displacement guide means for at least one mobile panel between a closed position in which the front of the mobile panel at least partly closes the opening, and an open position in which the mobile panel is located at the side of the opening. According to the invention, the mobile panel comprises:

a reception structure for a man-machine interface for which the facade is accessible when the mobile panel is in the closed position, and reception structure displacement means assuring that when the mobile panel is in the open position, the facade of the man-machine interface is moved towards the opening so that an operator placed in front of the opening can access the opening and the man-machine interface at the same time.

According to a first variant of embodiment, the reception structure displacement means are composed of displacement guide means that slide and pivot the mobile panel, thus ensuring that the mobile panel facade is facing the opening when the mobile panel is in the open position.

According to a second variant of embodiment, the reception structure displacement means are composed of means capable of pivoting the man-machine interface ensuring that the facade of the man-machine interface is accessible when the mobile panel is in the closed position or the open position.

Various other characteristics will become clear after reading the description given below with reference to the attached drawings that show different embodiments of the object according to the invention as non-limitative examples.

Figure 1:
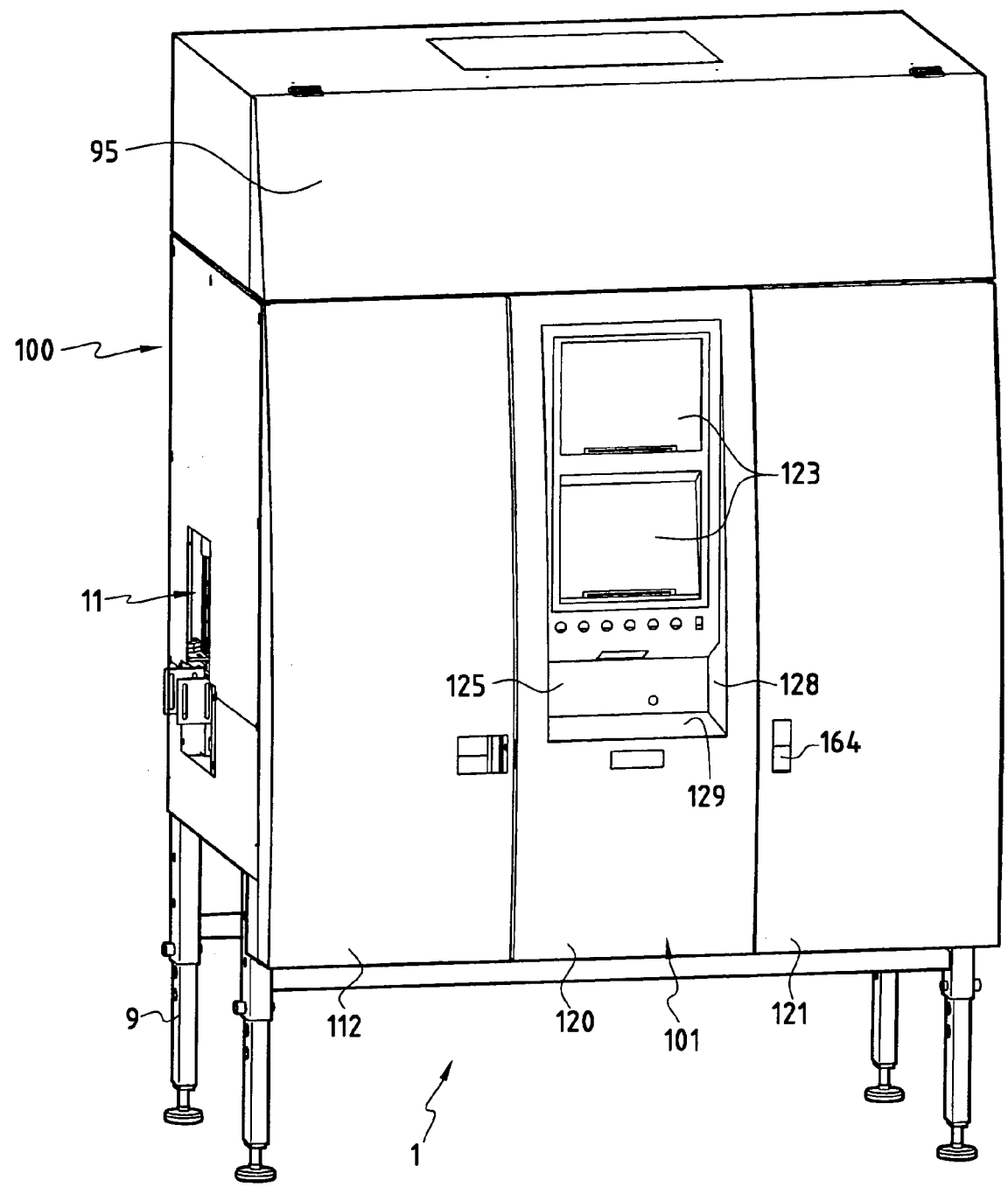
FIG. 1 is a perspective view of a machine according to the invention in the door closed position.
Figure 2:
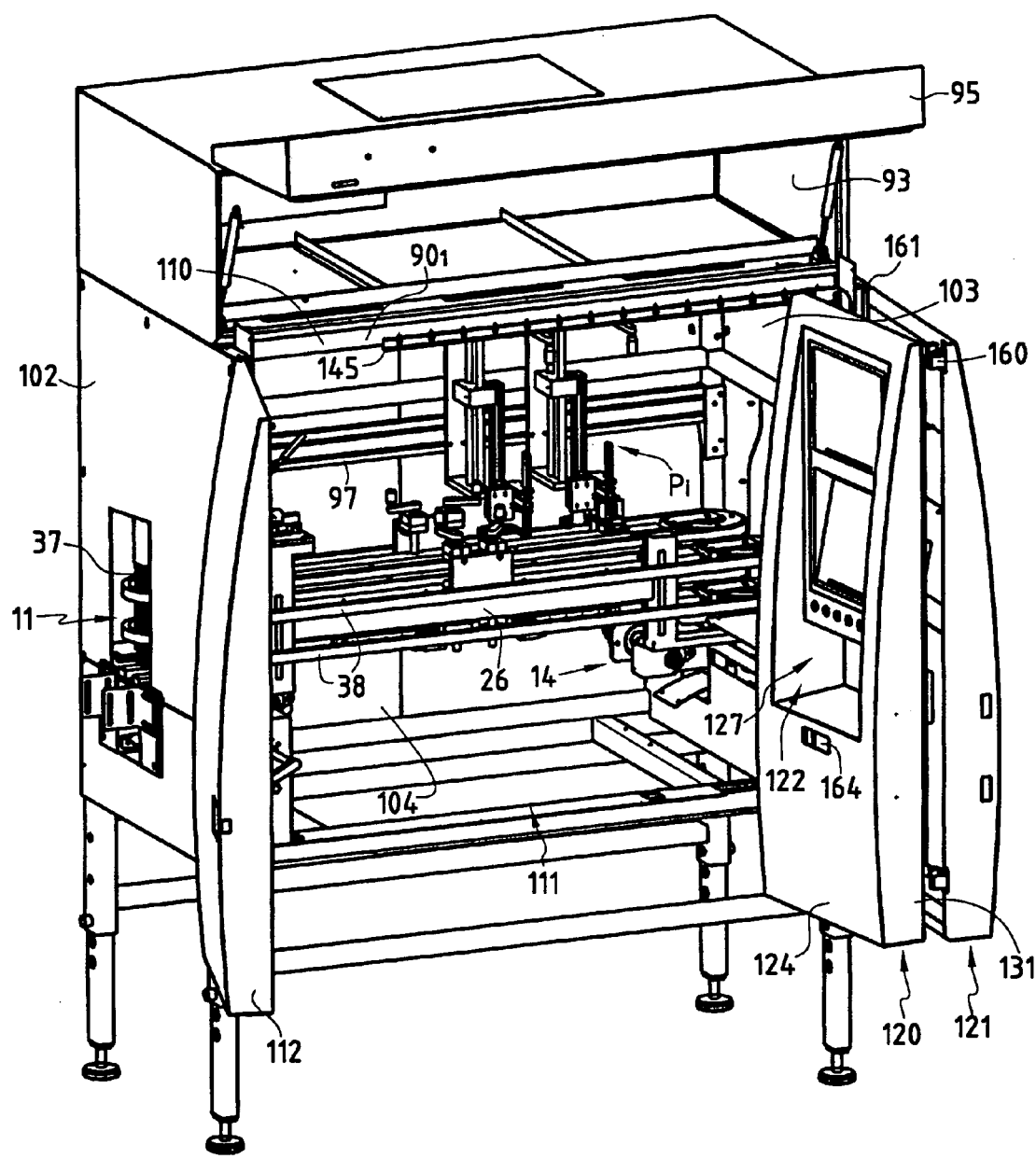
FIG. 2 is a view similar to FIG. 1 but shown with the door in the open position.

As shown more precisely in FIGS. 1 to 4, the subject of said invention relates to a machine 1 capable of moving receptacles (not shown) of all types, such as bottles, jars, pots, in front of at least one and more generally a series of receptacle checking and/or inspection stations Pi, some components of which are shown in FIG. 2. Each checking and/or inspection station comprises components such as supports, sensors, light sources, etc., in a known manner. Checking and/or inspection stations are not described more precisely since they are not included in the invention and are well known to those skilled in the art.

Said machine 1 will be inserted on a receptacle conveyance line such that on the input side of the machine 1, it comprises a conveyor 2 bringing receptacles to the machine 1, and on the output side a conveyor 3 removing receptacle from the machine 1. Conventionally, the machine 1 according to the invention will accept receptacles brought in by the conveyor 2 and the displacement of receptacles as far as the evacuation conveyor 3.

Figure 3:
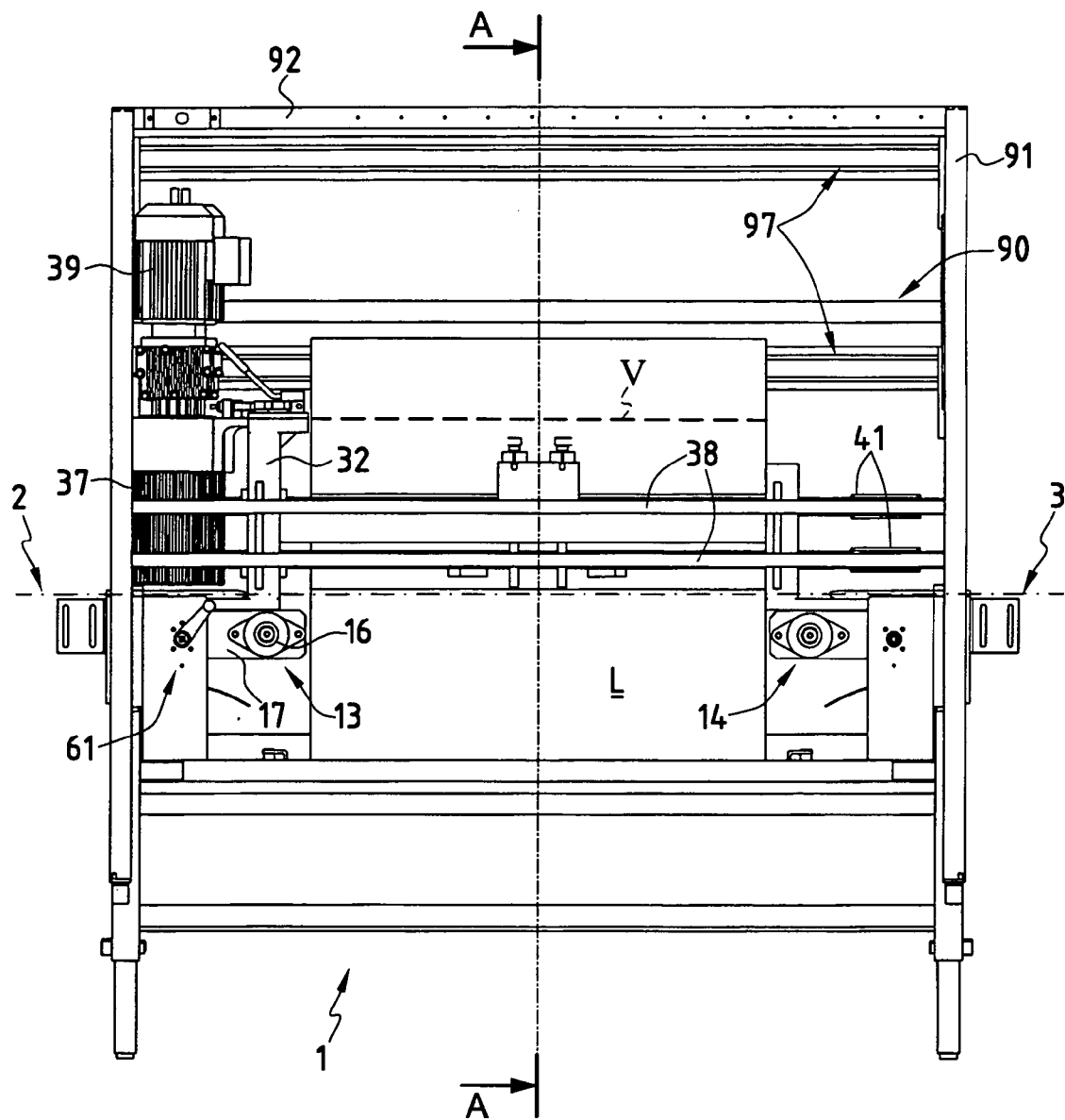
FIG. 3 is a front elevation view of a machine according to the invention without a door.
Figure 5:
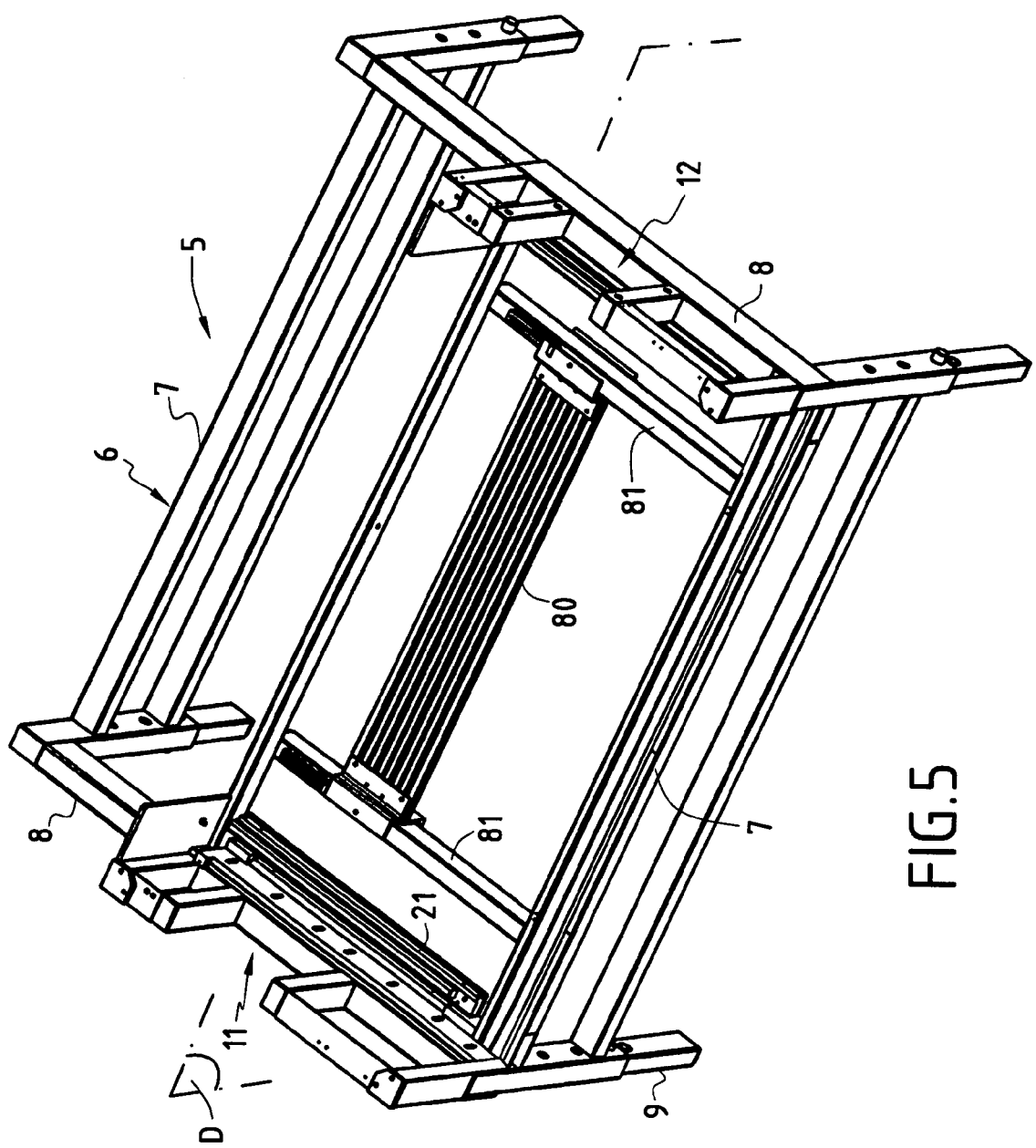
FIG. 5 is a perspective view of the lower frame forming part of the machine according to the invention.

As shown more particularly in FIG. 5, the machine according to the invention comprises a lower frame 5 delimiting a supporting frame 6 with two longitudinal sides 7 and two transverse sides 8, all in respect of the receptacle displacement plane D. Preferably, the supporting frame 6 is equipped with four stands 9 advantageously adjustable in height by any known means. Preferably, the transverse sides 8 are adjustable in length such that the machine 1 has an adjustable depth. This is possible because the transverse sides 8 are made of telescopic elements;

Each transverse side 8 has a passage compartment 11, 12 for the end of a receptacle input conveyor 2 and output conveyor 3 that are only shown diagrammatically in FIG. 3. Each input conveyor 2 and output conveyor 3 will cooperate with a return head, on the input side 13 and the output side 14, respectively installed on the lower frame 5. Conventionally, each conveyor 2, 3 is made using an endless conveyor belt fitted on a pulley 16 forming part of a return head 13, 14. Each pulley 16 is installed on a clevis 17 supported by a transverse side 8 of the lower frame 5. Therefore, it must be understood that the lower frame 5 delimits a passage compartment 11, 12 starting from each transverse side 8, in other words it delimits a volume in which a return head 13, 14 can be installed and in which a conveyor 2, 3 and receptacles carried by the conveyors can pass. Note that the return heads 13, 14 delimit a conveyance interruption volume V, in other words between conveyors 2, 3, forming the conveyance path. The width of said conveyance interruption volume V is the distance between the two return heads 13, 14, its depth is sufficient so that the largest diameter receptacle can pass, and its height is sufficient so that the tallest receptacle can pass.

According to one characteristic of the invention, each transverse side 8 is provided with a linear guide system 21 extending outside the conveyance interruption volume V. In the example shown, the guide systems 21 are formed by linear guide rails installed parallel to each other along a direction transverse to the displacement plane D of the receptacles passing through the return heads 13 and 14 of the conveyors 2, 3.

Figure 6:
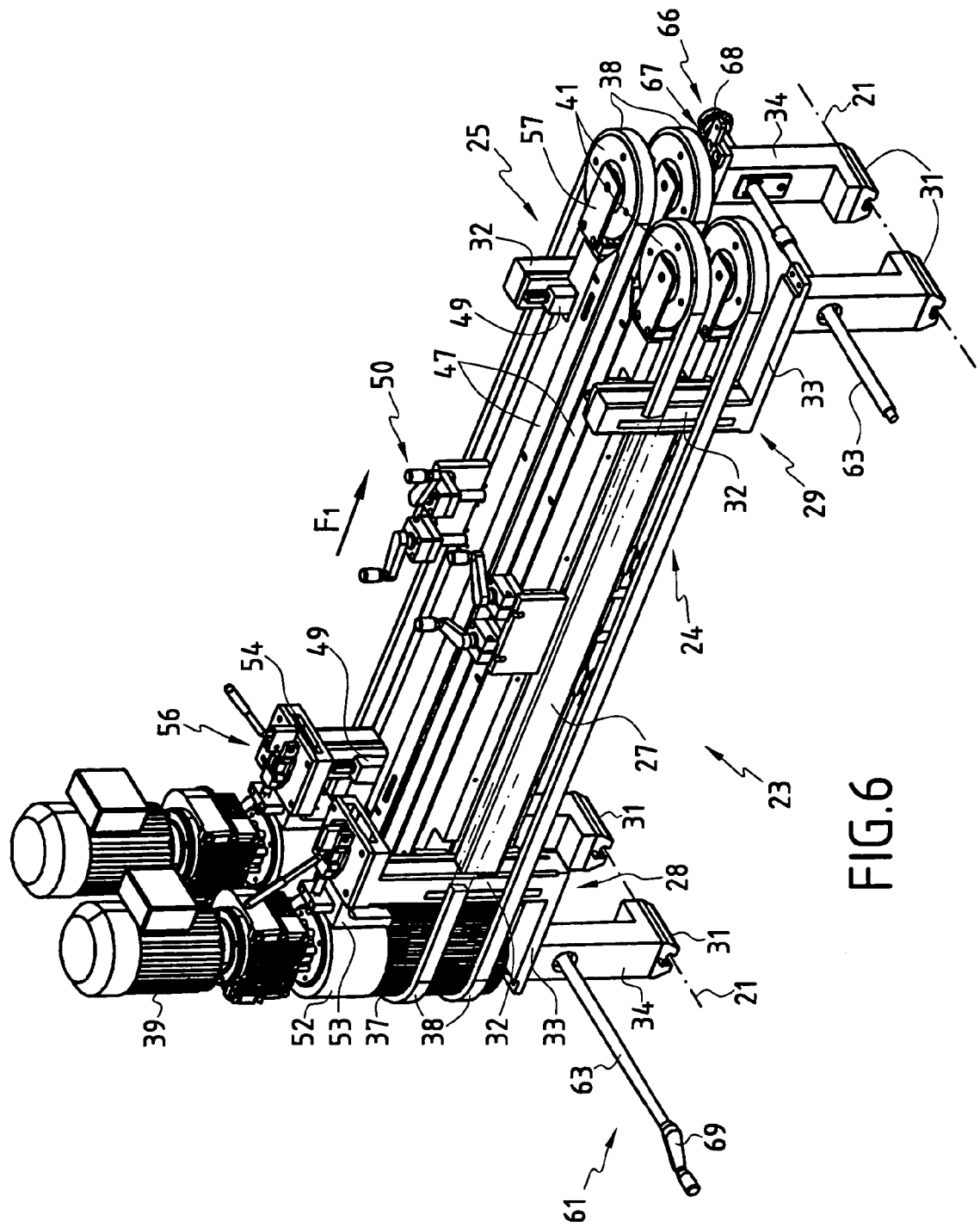
FIG. 6 is a perspective view of the mobile carriage forming part of the machine according to the invention.

As shown in FIG. 6, the machine according to the invention comprises a mobile carriage 23 supported by linear guide rails 21. The mobile carriage 23 is composed of a front half-carriage 24 and a back half-carriage 25, in the front and back of the machine 1. The half-carriages 24, 25 are symmetric about the displacement plane D.

Figure 7:
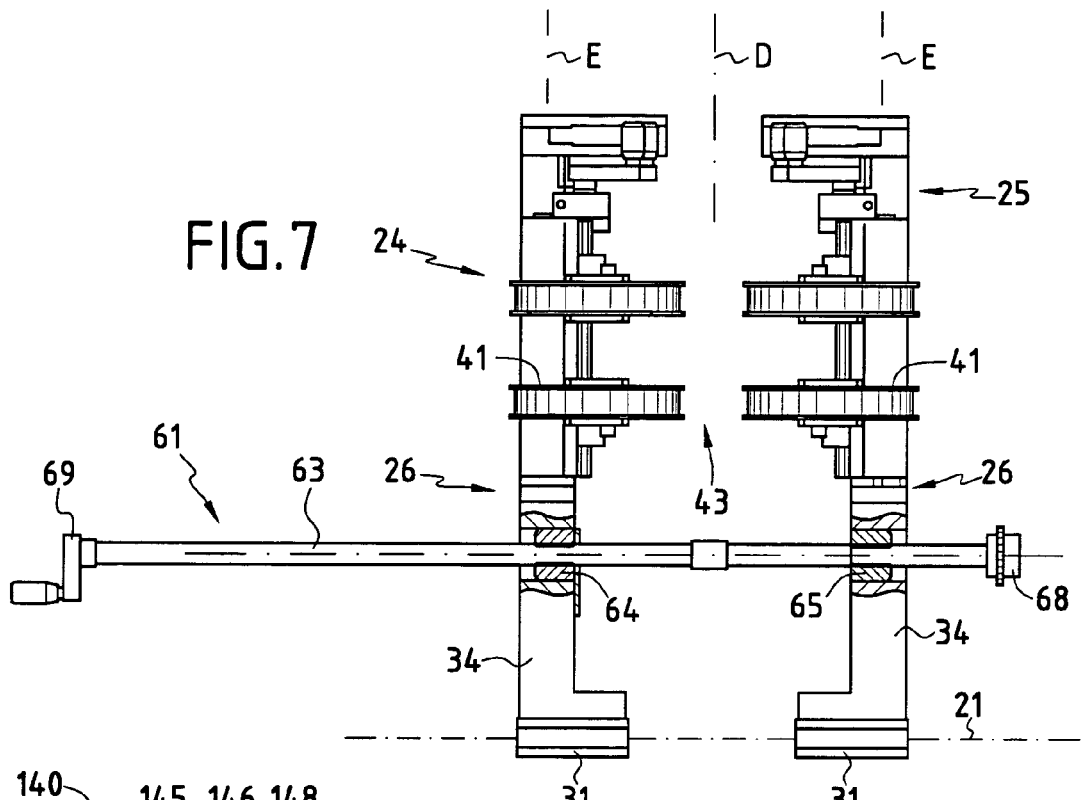
FIG. 7 is a cross-sectional view of the mobile carriage shown in FIG. 6.
Figure 8:
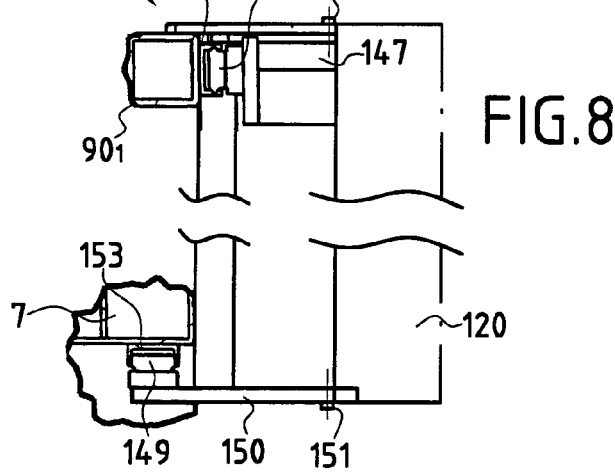
FIG. 8 is a detailed partial view showing the characteristics of the machine according to the invention.

Each half-carriage 24, 25, comprises a rigid bridge 26 installed at each end and sliding on the linear guide rails 21. Each rigid bridge 26 of the half-carriages 24, 25 is located in a longitudinal extension plane E parallel to the displacement plane D of the bottles (FIG. 7).

According to one preferred embodiment, each rigid bridge 26 is formed from a horizontal beam 27 supported at an upstream end by a support arm called the upstream support arm 28, and at a downstream end by a support arm called the downstream arm 29. Each support arm 28, 29 is provided with a means of cooperation with the linear guide system 21, such as a sliding pad 31 cooperating with a linear guide rail 21.

According to a preferred embodiment shown in the figures, each support arm 28, 29 is composed of a bracket with a vertical leg 32 connected to the horizontal beam 27 and a horizontal leg 33. The horizontal legs 33 in a particular rigid bridge 26 are installed top to bottom and face the transverse side 8 adjacent to the lower frame 5. Each rigid bridge 26 formed from a horizontal beam 27 extended by a bracket at each end is generally in the shape of an omega.

According to one preferred embodiment, each rigid bridge 26 is fitted with an upright 34 connected to the end of the horizontal leg 33 opposite the end to which the vertical leg 32 is connected, at each support arm 28, 29. Each upright 34 that is vertical and approximately parallel to a vertical leg 32 is fitted with a sliding pad 31 at its base.

As can be seen more precisely in FIG. 6, each upright 34 of the front half-carriage 24 installed facing an upright 34 of the back half-carriage 25 is installed at a distance from the other upright, the two uprights delimiting part of the straight transverse section of the passage compartment 11, 12. Said part of the passage compartment 11, 12 extends approximately over a length equal to the length delimited by the horizontal legs 33 so as to form an assembly volume for a return head 13, 14.

Each half-carriage 24, 25 also comprises a motorised device 37 driving at least one endless belt 38 in rotation, and in the example shown two endless belts. Each motorised drive device 37 is supported by the rigid bridge 26 located at a first end, namely in the example shown, the upstream end of the said bridge 26, such that the motorised devices 37 are located outside the conveyance interruption volume V. Advantageously, each half-carriage 24, 25 comprises a geared motor 39 installed on the centre-line of the motorised drive device 37, preferably composed of a drum or a drive sprocket common to the two endless belts 38. Therefore each drive drum 37 is in line with a geared motor 39, which limits their size. In the example shown, the motorised drive devices 37 are installed in the volume delimited by and between the upstream support arm brackets 38. More precisely, each drive drum 37 is approximately along the same line as an upright 34 over a height approximately the height of the vertical leg 32 of a support arm 28, each geared motor 39 installed along the line of a drive drum 37 projecting from the vertical leg 32 of the support arm 28. Note that the endless belts 38 extend over a limited length superposed with the input side conveyor 2, such that the receptacles brought in by the conveyor 2 can be handled by the belts 38.

Each half-carriage 24, 25 also comprises at least one return device 41 for an endless belt 38; in the example shown there are two of these return devices. The return devices 41 of each half-carriage are supported by the rigid bridge 26 of the said carriage, and are located at the output end of the said bridge opposite the upstream end equipped with the drive drum 37, such that the return devices 41 are located outside the conveyance interruption volume V. Preferably, each return device 41 is composed of a return pulley. In one example preferred embodiment, the return devices 41 are installed in the volume delimited by and between the brackets of the output side support arms 29. Therefore the return pulleys 41 are approximately vertically above the surface generated by the horizontal legs 33 of the output side support arms. Therefore the endless belts 38 extend over a limited length superposed with the conveyor 3 on the output side, such that the receptacles displaced by the endless belts 38 are picked up by the evacuation conveyor 3, at the return devices 41. The spindle of the return heads 13, 14 of the conveyors 2, 3 are thus located at the same level, or preferably within the interval delimited by the centre line of the motorised displacement device 37 and the spindle of the return pulley 41. Therefore, the receptacles will move between the motorised displacement device 37 and the return pulleys 41 along a displacement direction represented by the arrow $F_1$. Obviously, the direction of movement of the receptacles (from left to right on the drawings) may be in the direction opposite to that shown (by making a machine symmetrical with the machine described).

Thus, each half-carriage 24, 25 comprises at least one endless belts 38, each of them being installed between the motorised drive device 37 and a return pulley 41; in the example shown, there are two endless belts. Note that the two strands of each endless belt 38 extend on each side of the rigid bridge 26, in other words more precisely the beam 27 and the vertical leg 32 of each support arm 28, 29. Therefore, each endless belt 38 surrounds a rigid bridge 26 supported at its base by the lower frame 5 such that each endless belt 38 can be put into place or removed from the motorised drive device 37 and from the return device 41 from the top part of the half-carriages 24, 25.

Each endless belt 38 in a half-carriage has one strand along a line at a distance from a strand of an endless belt 38 carried by the other half-carriage, so as to delimit a receptacle gripping and movement path 43 between them. Each half-carriage 24, 25 is equipped with at least one bearing plate 47, each running behind a strand of a belt 38, and between the motorised drive device 37 and a return pulley 41, so as to define the gripping path 43; there are two of these bearing plates in the example shown.

According to one preferred embodiment, each bearing plate 47 is fitted with a return pulley 41 at its end installed on at least one, and preferably two guide slides 49 along a vertical direction and supported by the rigid bridge 26. Each bearing plate 47 is controlled in vertical translation on slides 49 using a control device 50 that regulates the height of each endless belt 38. Said type of adjustment gives optimum positioning of belts on receptacles as a function of their shape and/or their size. For example, each bearing plate 47 is moved by a manual control 50 acting on a screw-nut type system.

According to one preferred manufacturing characteristic, each motorised drive device 37 associated with a geared motor 39 forms a traveller installed free to slide on a rigid bridge along a direction approximately parallel to the direction of movement $F_1$ so that the endless belts 38 can be assembled and disassembled. Each motorised drive device 37 is provided with a support and guide bearing 52 also supporting the geared motor 39. Said type of support and guide bearing 52 is provided with a slide 53 capable of moving in translation inside a guide 54 supported by the top end of the vertical leg 32 of the input side support arm 28. Said type of mobile traveller is locked in position by a belt tensioning system 56 locking the traveller in the belt tensioned position. For example, the mobile traveller tensioning and locking system is of the toggle fastener type. Furthermore, each return device 41 is installed on a bearing plate 47 by means of a system 57 for tensioning an endless belt 38. Said type of tensioning system 57 may be made by a spring type system to accommodate variations in the length of endless belts 38.

The machine 1 according to the invention also comprises a system 61 for moving one half-carriage 24 away from or towards the other half-carriage 25. Said type of displacement system 61 is located outside the conveyance interruption volume V so that access to the said volume is left free.

According to one preferred embodiment, the displacement system 61 consists of two screw-nut systems, each system installed between the adjacent ends of the two rigid bridges 26 of the two half-carriages 24, 25. As shown in FIG. 7, each screw-nut system comprises a threaded rod 63 that at least partly cooperates with a first nut 64 installed in each upright 34 of the support arm of the front half-carriage 24 and with a second nut 65 installed in each upright 34 of the support arm of the back half-carriage 25. The nuts 65 fitted on the back half-carriage 25 have a thread in the direction opposite to the direction of the nuts 64 of the front half-carriage 24, such that rotation of the threaded rods 63 in a particular direction causes the two half-carriages to move towards each other or away from each other. Note that the threaded rods 63 move into the volume of the passage compartments 11, 12, without hindering the displacement of receptacles, since the threaded rods 63 are inserted between the strands of the conveyors 2, 3.

The movement of the two threaded rods 63 is synchronised by a transmission 66, for example a chain transmission, extending parallel to the longitudinal extension plane E. In the example shown, the transmission 66 is composed of a chain 67 engaged on two gears 68 fixed on the ends of each threaded rod 63 projecting from the rigid bridge 26 of the back half-carriage 25. One of the threaded rods 63 is provided with a rotation control device 69, for example such as a handle, enabling simultaneous rotation of the two threaded rods 63, due to the transmission 66. In said example of embodiment, the system 61 controlling movement of the half-carriages towards or away from each other controls simultaneous and identical displacement of the two half-carriages 24, 25 that remain centred about the displacement plane D along the middle of the gripping and displacement path 43 of the receptacles.

According to one variant of embodiment, the system 61 controlling movement of the half-carriages towards or away from each other controls movement of one of the half-carriages with respect to the other kept in the fixed position. In this respect, each screw-nut system is provided with a device for selecting the method of moving the half-carriages with respect to each other, namely a centred displacement or an offset displacement from the displacement plane D. Said type of selection device declutches one half-carriage with respect to the threaded control rods 63. for example, the nuts of a half-carriage, for example the back half-carriage, are provided with a solidarisation pin with respect to the upright 34. Said solidarisation pin is removable such that the nuts are installed free to rotate. When these solidarisation pins are withdrawn, the rotation of the threaded control rods 63 causes free rotation of the nuts, such that the corresponding half-carriage does not move.

Figure 5A:
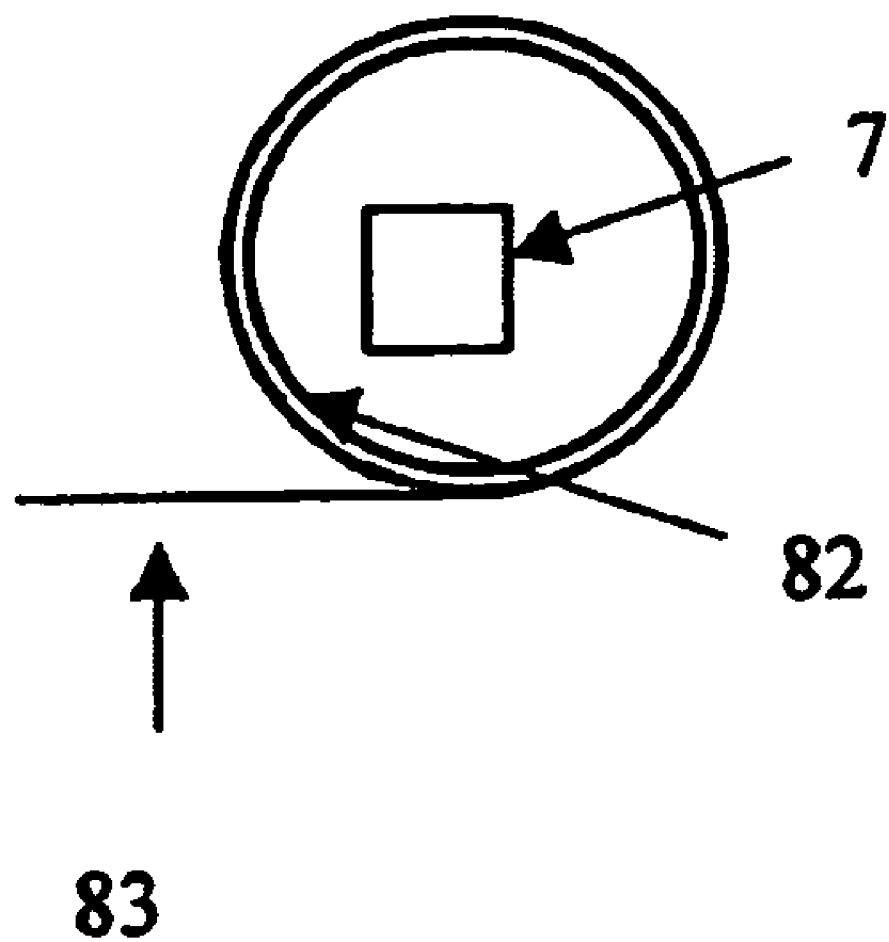
FIG. 5a is a schematic view showing the curtain and drum associated with back edge of frame 7 in FIG. 5.

According to another preferred embodiment of the invention, the lower frame 5 is equipped with a longitudinal support plate 80 installed free to slide on two cross pieces 81 supported by the longitudinal sides of the frame and extending parallel to the transverse sides 8. The plate 80 that extends at a distance from the rigid bridges 26 will support the elements forming part of the checking and/or inspection stations of receptacles carried by the endless belts 38. For example, these elements may be composed of supports, lighting sources, optical sensors, etc. The sliding assembly of said support plate 80 enables a complete displacement of all devices supported by it. Preferably, said support plate 80 is provided with means of locking it in position on the cross pieces 81. According to one advantageous embodiment as shown in FIG. 5A, the support plate 80 is connected to a curtain, shutter or mat 83 wound around a drum 82 installed on the longitudinal back edge 7 of the frame. It must be understood that between the back longitudinal edge and the support plate 80, the curtain forms a reception or direction guidance mat for different objects that could fall from the machine, for example such as glass debris.

According to another preferred characteristic of embodiment, the machine 1 comprises an upper frame 90 supported by the lower frame 5 and made of four uprights 91 supported on the supporting frame 6 of the lower frame 5. The four uprights 91 are connected at the top part by a frame 92 designed to support a storage compartment 93 provided with an access door 95 on the facade. Said type of compartment 93 is adapted to contain all electrical and electronic equipment necessary for operation of the machine and the control stations Pi.

The two back uprights 91 support one or two back longitudinal beams 97, extending horizontally and designed to support elements forming part of the checking and/or inspection stations Pi. Preferably, these support beams 97 are installed on the upper frame 90 on transverse slides controlling their movements towards and away from the longitudinal extension plane E in which they are located.

Figure 4:
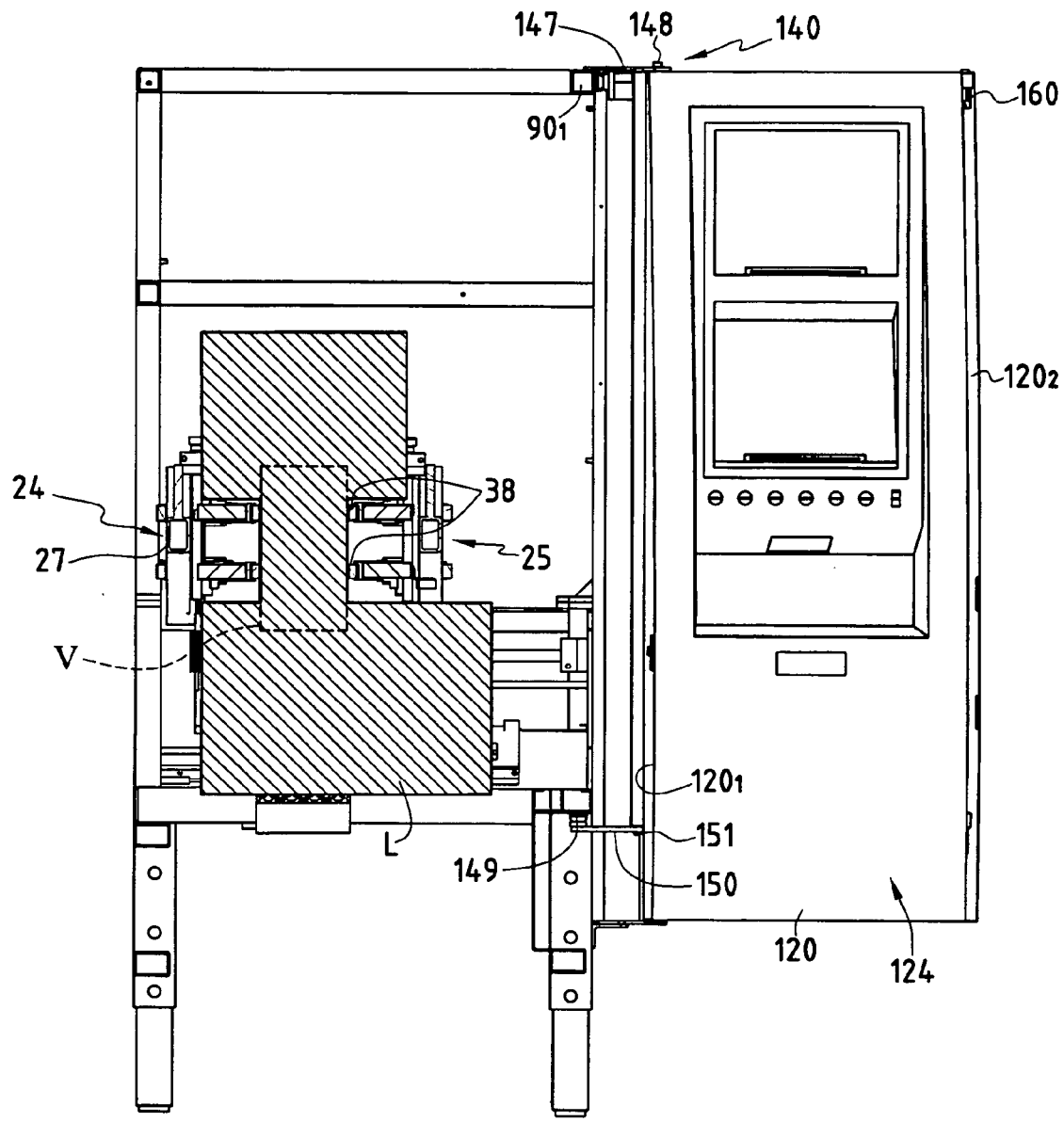
FIG. 4 is a cross-sectional view in elevation taken approximately along lines A—A in FIG. 3, of the machine equipped with a door in the open position.

As should be clear from the above description, the machine 1 according to the invention is compact, and there is a free space around the conveyance interruption volume V, shown diagrammatically as reference L in FIGS. 3 and 4. Therefore, it must be understood that the structure of machine 1 is designed to facilitate access around the conveyance interruption volume V, so that the maximum number of checking and/or inspection stations Pi can be placed in it. The drawings quite clearly show that said machine 1 has a maximum free space L around the conveyance interruption volume V, and also fulfils its function of handling and moving receptacles.

As can be more clearly seen in FIGS. 1 and 2, the machine 1 according to the invention preferably comprises a protection cladding 100 and an access door 101. The protection cladding 100 consists of side panels 102 and 103 supported by the transverse sides 8 of the lower frame 5 and the upper frame 90 in which openings are formed corresponding to the passage compartments 11, 12 for the receptacle input conveyor 2 and the receptacle output conveyor 3. The protection cladding 100 also comprises a series of back panels 104 cladding the back of the machine. The machine 1 also comprises a chassis 110 on the facade delimiting an opening 111 through which the machine can be accessed. Said opening 111 is opened or closed using a door 101 according to the invention, and corresponding to a pivoting flap 112, in the example shown. In the example shown in the drawings, the door 101 comprises a first mobile panel 120 installed hinged to a second mobile panel 121.

According to one characteristic of the access door 101 according to the invention, the first mobile panel 120 comprises a reception structure 122 for instrumentation and/or control means for controlling the machine 123. These instrumentation and/or control means 123 make up a man-machine interface and are in the form of a keyboard, a screen, a control desk, a mouse, etc. Said man-machine interface 123 is provided with a facade that is easily accessible from the facade 124 in the first mobile panel 120 when it is in the position to close the opening. As is quite clear in FIG. 2, the thickness of the first mobile panel 120 is preferably such that instrumentation and/or control means 123 can be installed. Consequently, the first mobile panel 120 has a back wall 125 and the facade wall 124 is at a distance from said back wall, and at least one housing 127 delimited by the side plates 128 connected to a plane wall 129 is formed in said facade wall. The back wall 125 is connected to the facade wall 124 through two outer sides 131, such that the first mobile panel 120 forms a closed box within the thickness of which the man-machine interface 123 is installed.

According to another characteristic of the access door 101, the chassis 110 is fitted with displacement guide means 140 for the mobile panels 120, 121, so as to move the mobile panels between a closed position in which the facade 124 of the first mobile panel 120 at least partly closes the opening (FIG. 1), and an open position in which the mobile panels 120, 121 extend laterally from the opening 111.

According to another characteristic of the invention, the mobile panel 120 comprises reception structure displacement means 122 adapted so that when the mobile panel is in the open position, the facade of the man-machine interface 123 is facing towards the opening so that an operator in front of the opening 111 can access the opening and at the same time access the man-machine interface 123. Therefore, it must be considered that when the door is in the closed position, an operator can access the instrumentation and control means 123 without them taking up any space surrounding the machine 1. When the opening 111 is in the open position, an operator in front of the opening can access instrumentation and/or control means 123 while viewing the inside of the machine without changing position, so that for example he can observe the result of controls made on the man-machine interface 123 at the same time. Furthermore, there is no limit on access to the opening 111, except for the thickness of the mobile panels 120, 121.

In the preferred embodiment shown on the drawings, the reception structure displacement means 122 are composed of means 140 of guiding movements of the mobile panel that slide and pivot the mobile panel 120 such that when the mobile panel is in the open position, the facade 124 of the mobile panel is facing the opening 111.

In the example embodiment in which there is one door with two mobile panels (FIGS. 1, 2, 4 and 8), the sliding and pivoting guide means 140 consist of at least one support and guide rail 145 installed on the longitudinal front side 90, of the top frame 90. A rail 145, called the upper rail, is provided with a <<C>> shaped prismatic transverse section and acts as a guide support for a roller device 146, such as a wheel. Said roller device 146 is connected to a tab 147 installed around a pivot 148 in the top part of the first mobile panel 120, at its free vertical end 120$_1$. The first mobile panel 120 is also equipped with a guide device 149 supported by a tab 150, installed on a pivot 151 in the bottom part of the first mobile panel 120, at its free vertical end 120$_1$. The guide device 149 is installed inside a rail 153, called the lower rail, supported by a longitudinal edge 7 of the lower frame 5 and with a <<U>> shaped prismatic transverse section.

Therefore in the above description, the first mobile panel 120 is suspended from the upper rail 145, while the lower rail 153 cooperating with the guide device 149 prevents rotation of the first mobile panel 120. Obviously, it would be possible to invert the position of the roller device 146 and the guide device 149 or to use two roller devices for support and guidance of the first mobile panel 120.

The first mobile panel 120 is installed hinged at its vertical end 120$_2$, opposite the free vertical end 120$_1$, by hinges 160 on a side of the second mobile panel 121 which is also installed hinged on the chassis 110 at its opposite side by hinges 161. Therefore the second mobile panel 121 is installed hinged at one end to the chassis 110 along a vertical direction passing through the axes 161, and at the other end to the first mobile panel 120 also along a vertical direction passing through the hinges 160.

As is clear from the above description, the mobile panels 120 and 121 can close the opening when they are in the deployed position. In said position, the front walls of the panels 120, 121 are positioned in line with each other and are facing outwards from the machine. When work has to be done on the machine 1, the door 101 is opened by pulling on at least one handle 164 placed for example on the second mobile panel 121, so as to fold the two mobile panels 120, 121 so that the first mobile panel 120 is folded in contact with the second mobile panel with their inner faces or bottom facing each other. In said position, the mobile panels 120, 121 are approximately perpendicular to the opening with the facade 124 of the first mobile panel 120 turned or oriented towards the opening 111. The door is moved from its open position to its closed position by taking the opposite steps, for example applying a tension force on the first mobile panel 120 starting from a handle 164 to make it move along the guide rails 145, 153.

Figure 9:
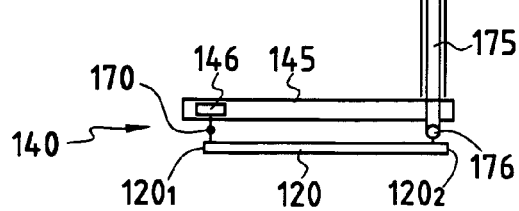
FIGS. 9 and 10 are diagrammatic views of another example of how a door comprising a mobile panel can be installed on a machine.
Figure 10:
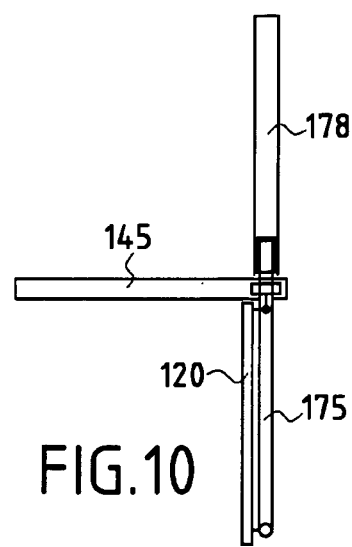

FIGS. 9 and 10 illustrate another variant of embodiment of the sliding and pivoting guide means 140 for an access door 101 comprising a single mobile panel 120. According to said variant of embodiment, the guide means 140 are composed of at least one and preferably two support and guide rails 145, 153 as described above, for rolling devices 146, 149 respectively installed on pivots 170 on a vertical end 120$_1$ of the mobile panel 120. The other vertical end 120$_2$ of the mobile panel 120 is connected by pivots 176 at its top and its bottom, to two extension bars 175 each guided in translation in a slide 178 fixed along a direction approximately perpendicular to the opening 111.

A tension force on the mobile panel 120 makes the roller devices 146, 149 slide on the rails 145, 153, simultaneously making the extension bar 175 extend so that the mobile panel 120 can be pivoted so that at the end of its movement distance, it is approximately perpendicular to the opening 111. The opening 111 is closed by making a movement of the mobile panel 120 in the inverse direction.

In the preferred embodiment described above, the reception structure displacement means 122 are composed of door displacement guide means so that the man-machine interface 123 can be positioned such that the facade is accessible equally well in the open and closed positions of the door. Note that the reception structure displacement means 122 may consist of reception structure pivoting means 122 such that the facade of the man-machine interface 123 is accessible in the closed and open positions of the mobile panel. In other words, these pivoting means provide a means of moving the facade of the man-machine interface 123 to the back of the mobile panel 120 in the open position of the mobile panel, so that the facade is facing the opening 111.

As will be clear from the above description, the displacement guide means are adapted so as to bring the facade of the man-machine interface 123, in the open position, into a position allowing access to the opening 111 and to the man-machine interface 123. In the open position, the mobile panel 120 is located laterally or on the side of the opening 111. In the example shown, the movement guide means enable the facade of the man-machine interface 123 to move into a plane approximately perpendicular to the plane delimited by the opening 111, when the mobile panel 120 is in the open position. In other words, these displacement means enable the facade of the man-machine interface 123 to move into a plane forming an angle with the plane delimited by the opening 111 equal to between 40° and 135°, and preferably between 60° and 110°, when the mobile panel in the open position.

Advantageously, the mobile panel 120 is locked in its open and close positions by any appropriate means.

The invention claimed is:

1. A machine for moving receptacles in front of at least one inspection station, along a given direction, said machine comprising:
   a lower frame supporting a front half-carriage and a back half-carriage extending along longitudinal planes parallel to each other, each half-carriage comprising:
   a motorized device for driving at least one belt in rotation, the motorized drive device being located at a first end of the half-carriage, at least one return device for at least one belt, located at the second end of the half-carriage, at least one first endless drive belt installed between the motorized drive device and the return device with one strand placed at a distance from the strand of the belt supported by the other half-carriage so as to delimit a receptacle gripping and movement path between them, wherein the lower frame has at least two transverse sides one of which has a passage compartment for the end of a receptacle input conveyor designed to cooperate with a return head on the input side, installed on the frame, while the other transverse side has a passage compartment for the end of a receptacle output conveyor designed to cooperate with a return head on the output side, installed on the frame, to delimit a volume interrupting the conveyance, each transverse side being provided with a linear guide system extending on the outside of the conveyance interruption volume, the front half-carriage and the back half-carriage comprising a mobile carrier, each half-carriage comprising a rigid bridge installed at each end, and sliding on the linear guide systems, and a displacement system connected to at least one of the half carriages and adapted to move one half-carriage away from or towards the other half-carriage, and located outside the conveyance interruption volume.

2. The machine according to claim 1, wherein each half-carriage comprises a geared motor installed on a centerline of the motorized drive device.

3. The machine according to claim 1, wherein each half-carriage comprises:

a second return device for a belt, supported by the rigid bridge (26) and being located at the second end of the said bridge and extending superposed from the first return device, each return device being composed of a pulley, and a second endless drive belt installed between the motorized drive device and the second return device with one strand of the belt passing in front of a bearing plate supported by the rigid bridge and at a distance from a strand of the second belt supported by the other half-carriage, and a common drive drum driving the first and second belts.

4. The machine according to claim 1, wherein each return device is supported by a bearing plate which is installed on at least a guide slide along a vertical direction and supported by the rigid bridge, each bearing plate being moved in vertical translation on the guide slide using a control device, so that the height of the belts can be adjusted.

5. The machine according to claim 1, wherein the rigid bridge of each half carriage is formed from a beam supported at each end by a support arm fitted with a pad cooperating with a linear guide system.

6. The machine according to claim 5, wherein each support arm is composed of a bracket with a vertical leg connected to the beam and a horizontal leg facing the transverse side to close to the frame and supported by an upright fitted with a pad at its base, the horizontal legs and the uprights of the half-carriages installed facing each other and defining part of a passage compartment for a conveyor.

7. The machine according to claim 6, wherein each bracket of a half-carriage installed facing a bracket of the other half-carriage defining a volume for installation of the motorized drive devices and the return devices.

8. The machine according to claim 1, wherein the system to move the half-carriages towards each other or away from each other comprises two screw-nut systems installed between the adjacent ends of the two rigid bridges, one of the systems being fitted with a movement control device and being connected to the other system through a transmission extending parallel to the longitudinal extension planes.

9. The machine according to claim 8, wherein movement of the half-carriages towards or away from each other controls movement of one of the half-carriages with respect to the other kept in the fixed position, each screw-nut system being provided with a device for selecting the method of moving the half-carriages with respect to each other, namely a centered displacement or an offset displacement from the displacement plane.

10. The machine according to claim 1, wherein:

each motorized drive device forms a traveller installed free to slide on the rigid bridge along a direction approximately parallel to the direction of movement, so that belts can be assembled and disassembled, said mobile traveller being locked in position by a belt tensioning and locking system, and each return device is installed on a belt tensioning system.

11. The machine according to claim 10, wherein the belt locking and tensioning system is of the toggle fastener type.

12. The machine according to claim 1, wherein the lower frame is equipped with a longitudinal support plate installed free to slide on two cross pieces supported by the longitudinal sides of the frame and extending parallel to the transverse sides, the plate being designed to support elements forming part of the at least one inspection station.

13. The machine according to claim 12, wherein the longitudinal support plate is connected to a curtain wound around a drum installed on the longitudinal back edge of the lower frame.

14. The machine according to claim 1, wherein the lower frame is equipped with four stands that are adjustable in height and are adapted to support a supporting frame for which the at least two transverse sides are adjustable in length.

15. The machine according to claim 1, wherein the lower frame supports an upper frame, the upper frame formed by four uprights connected at the top part by an additional frame, two of the uprights supporting at least one back longitudinal beam designed to support elements forming part of the at least one inspection station.

16. The machine according to claim 15, wherein the at least one back longitudinal beam is installed on the upper frame on transverse slides that are adapted to control movement of the at least one back longitudinal beam towards and away from a longitudinal extension plane.

17. The machine according to claim 15, wherein the upper frame defines a top compartment through an access door located on a facade of the machine.

18. The machine according to claim 1, further comprising a protection cladding and an access door.

19. The machine according to claim 18, wherein the access door comprises a chassis defining an opening, at least one mobile panel comprising a reception structure for instrumentation and/or control means for controlling the machine, and accessible from a facade of the mobile panel, and means for displacing the mobile panel and reception structure so that when the mobile panel is in the open position, the facade of the instrumentation and/or control means is facing towards the opening so that an operator in front of the opening, can access the opening and at the same time access the instrumentation and/or control means.

20. The machine according to claim 19, wherein the means for displacing the mobile panel and reception structure are composed of means for sliding and pivoting the mobile panel such that when the mobile panel is in the open position, the facade of the mobile panel is facing the opening.

21. The machine according to claim 19, wherein the means for displacing the mobile panel and reception structure are composed of a means for pivoting the reception structure for a man-machine interface such that a facade of the man-machine interface is accessible equally well in the open and closed positions of the mobile panel.

22. The machine according to claim 19, wherein the means for displacing the mobile panel and reception structure enables the facade of the mobile panel to move into a plane forming an angle with the plane defined by the opening, equal to between 40° and 135° and preferably between 60° and 100°.

23. The machine according to claim 19, wherein the means for displacing the mobile panel and reception structure enables the facade of the reception structure to move into a plane approximately perpendicular to the plane delimited by the opening.

24. The machine according to claim 19, wherein the means for displacing the mobile panel and reception structure allow the mobile panel to slide and pivot, and comprise at least one support and guide rail for at least one roller device fitted on the mobile panel, the mobile panel being connected by a pivot at its top part and connected at its bottom part to an extension bar guided in translation along a direction approximately perpendicular to the opening.

25. The machine according to claim 19, wherein the means for displacing the mobile panel and reception structure comprise at least one support and guide rail for at least one roller device fitted on a first mobile panel hinged to a second mobile panel installed hinged on the chassis, the mobile panels being intended to fold in contact with each other in the open position of the opening.

26. The machine according to claim 24, wherein the means for displacing the mobile panel and reception structure comprise a support and guide upper rail arranged in a top part of the chassis and a guide lower rail arranged in a lower part of the chassis, one supporting the roller device(s) fitted on the mobile panel, and the other supporting a guide device.

27. A machine according to claim 8, wherein each screw-nut system comprises a threaded rod cooperating with a first nut installed in each support arm of the front half-carriage and with a second nut installed in each support arm of the back half-carriage, the nuts fitted on the back half-carriage having a thread in the direction opposite to the direction of the nuts of the front half-carriage, such that rotation of threaded rod in a particular direction causes the two half-carriages to move towards each other or away from each other and to remain centered about the displacement plane along the middle of the gripping and displacement path of the receptacles.

* * * * *